United States Patent [19]

Calhoun et al.

[11] Patent Number: 5,388,972
[45] Date of Patent: Feb. 14, 1995

[54] PERISTALTIC PUMP WITH REMOVABLE TUBING OF PRECISE LENGTH

[75] Inventors: Jeffrey E. Calhoun, Pleasantville; Timothy F. Wickham, Nanuet, both of N.Y.

[73] Assignee: Medical Laboratory Automation, Inc., Pleasantville, N.Y.

[21] Appl. No.: 208,638

[22] Filed: Mar. 9, 1994

[51] Int. Cl.⁶ .................................................. F04B 93/08
[52] U.S. Cl. ................................................ 417/477.11
[58] Field of Search .................................. 417/474–478

[56] References Cited

U.S. PATENT DOCUMENTS

| | | | |
|---|---|---|---|
| 3,841,799 | 10/1974 | Spinosa et al. | 417/475 |
| 3,927,955 | 12/1975 | Spinosa et al. | 417/477 |
| 4,138,205 | 2/1979 | Wallach | 417/477 J |
| 4,179,249 | 12/1979 | Guttman | 417/477 J |
| 4,187,057 | 2/1980 | Xanthopoulos | 417/63 |
| 4,493,706 | 1/1985 | Borsanyi et al. | 604/153 |
| 4,519,754 | 5/1985 | Minick | 417/477 J |
| 4,527,323 | 7/1985 | Dawson | 417/477 R |
| 4,585,399 | 4/1986 | Baier | 417/477 K |
| 4,673,334 | 6/1987 | Allington et al. | 417/53 |
| 4,886,431 | 12/1989 | Soderquist et al. | 417/477 |
| 4,925,376 | 5/1990 | Kahler | 417/477 J |
| 5,082,429 | 1/1992 | Soderquist et al. | 417/477 J |
| 5,213,483 | 5/1993 | Flaherty | 417/477 A |

*Primary Examiner*—Richard A. Bertsch
*Assistant Examiner*—Peter Kortnyk
*Attorney, Agent, or Firm*—Wolf, Greenfield & Sacks

[57] ABSTRACT

A precision peristaltic pump is provided which assures that a precisely controlled length of tubing is operated upon by the pump. Recesses are provided on either side of a tube receiving gap for the pump, which recesses have different sizes and/or shapes and fittings are provided on the tubing on either side of a precisely determined length of tubing, which fittings are sized and/or shaped so as to only fit in one of the recesses in only a single orientation. This assures that the orientation of the tubing in the pump gap is always the same. The fittings may be a block which is formed on the tubing itself and of the same material as the tubing or may include a stop of a harder material, such as a hard plastic, mounted to or sandwiching each block. The pump is designed so that if one of the fittings is not fully seated in the corresponding recess, the projecting fitting interacts with a cover or other element of the pump to prevent the pump from being moved to its operative position.

16 Claims, 4 Drawing Sheets

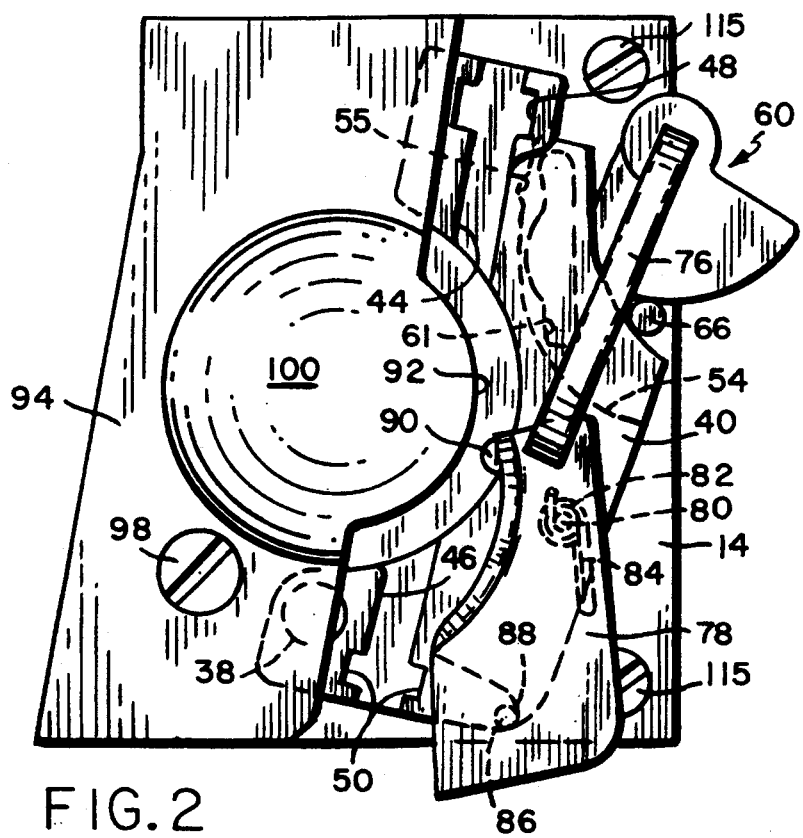
FIG. 2
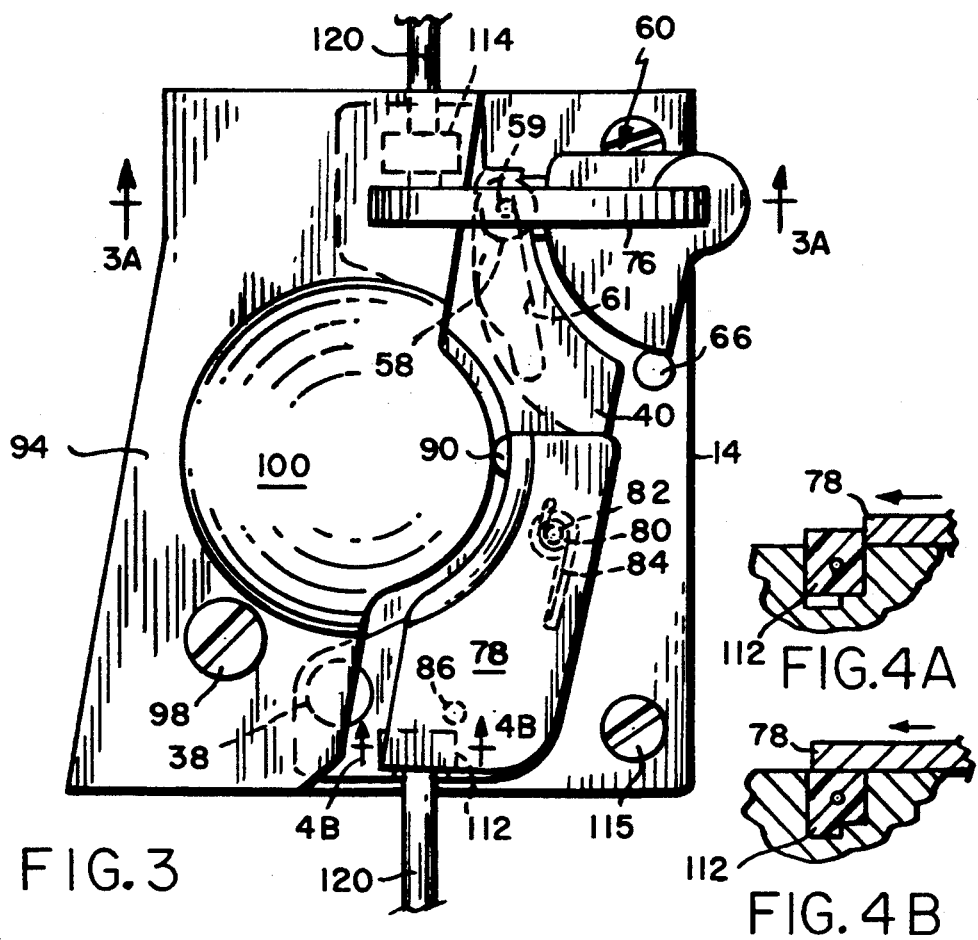
FIG. 3
FIG. 4A
FIG. 4B

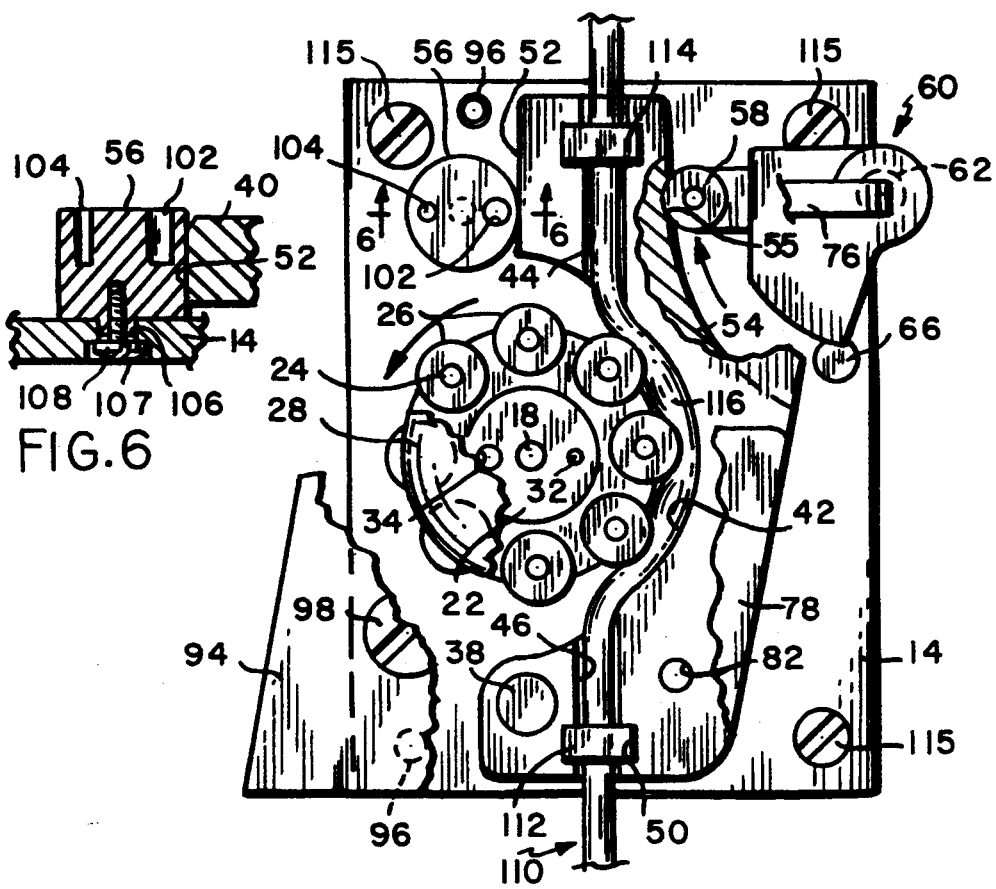
FIG.6
FIG. 5
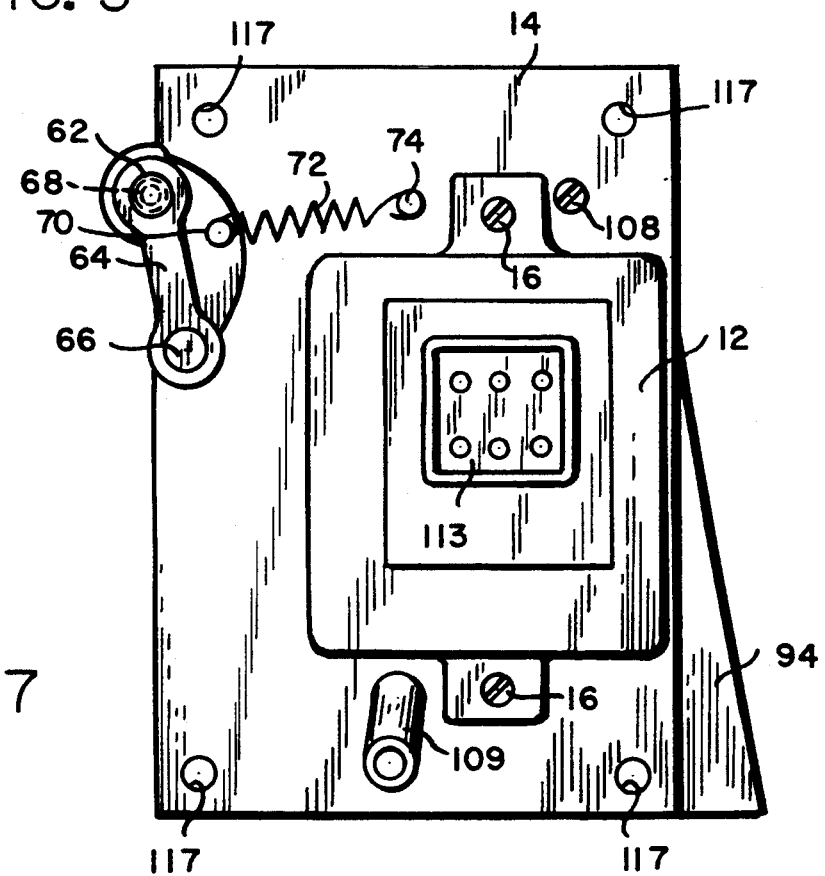
FIG.7

PERISTALTIC PUMP WITH REMOVABLE TUBING OF PRECISE LENGTH

FIELD OF THE INVENTION

This invention relates to peristaltic pumps and more particularly to enhanced precision for such pumps by precise control of the length and orientation of tubing being operated on by the pump.

BACKGROUND OF THE INVENTION

There are various applications where it is necessary to pump a relatively small and very precise volume of a fluid which may contain viscous material (i.e. higher viscosity or gooey material). An example of such application is in a medical laboratory where a reagent which contains protein needs to be pumped from a reservoir cup to an analyzer cuvette, generally through a heat exchanger, for performing coagulation analysis. In such applications, the viscous material tends to build up and accumulate on the various parts of the pump which are in contact with the fluid. Such buildup can cause contamination of future samples passed through the pump and can also cause slight alterations in the quantity of fluid being passed through the pump, which variations are unacceptable when measurements to microliter precision are required. However, such materials tend to cling tenaciously to pump parts and are hard to wash off without disassembly of the pump.

One way around this problem is to use peristaltic pumps for pumping such fluids, the fluid in such pumps passing through a tube and not coming in contact with any of the pump parts. The tubing through which the fluid flows is easily removed for cleaning and is generally relatively inexpensive so that contaminated tubing may be replaced where either initial cleaning or further cleaning is not possible, or is not economically feasible.

However, the length of the flexible tube which is operated on by the pump in existing peristaltic pumps cannot be precisely controlled, leading to variations in the volume of the fluid being pumped for each pump revolution. Even if the pump is calibrated for a particular piece of tubing, if that piece of tubing is removed (either for cleaning, to prevent contamination when the pump is used for a different sample or reagent, or for other purposes) the set which the tube inherently takes when in the pump will cause volume variations unless the tube is replaced in exactly the same orientation as the tube had when the calibration was performed. To the extent the tubing has seams, which is the case for many types of tubing used with such pumps, contact of the seams with the operating parts of the pump may also cause slight variations in pumped volume, this being another reason why consistent tube orientation is desirable. However, current peristaltic pumps do not have a facility for assuring such consistent orientation of the tubing.

While the variations in pump volume caused by slight variations in the length of the tubing operated on by the pump are not great, and do not create problems in many applications, such volume variations have made use of peristaltic pumps undesirable in applications where precise pump volumes, accurate to within a few microliters, are required. A need therefore exists for an improved peristaltic pump which is capable of pumping fluids with precision in the microliter range, and in particular which is capable of precisely controlling the length and orientation of the tubing acted upon by the pump so as to facilitate such precision pumping.

SUMMARY OF THE INVENTION

In accordance with the above, this invention provides a precision peristaltic pump which utilizes a plurality of rollers mounted at spaced intervals along the periphery of a circular member. A motor rotates the circulate member through a precise number of fractional rotations and a platen is provided having a curved surface facing the rollers, the curve of the curved surface being complementary to that of the member-mounted rollers. The member and platen are mounted such that they are movable relative to each other between an inoperative position where they are substantially spaced from each other and an operative position where there is a small, precise gap between the platen and a selected number of adjacent rollers. For a preferred embodiment, only the platen is moved to move the member and platen between their operative and inoperative positions and a stop is provided for precisely defining the operative position of the platen. The platen is preferably latched in its operative position.

First and second recesses are formed on opposite sides, respectively, of the gap, the recesses being sized and/or shaped differently so that a complementary fitting which fits in at least one of the recesses will not fit in the other. An element is provided for covering each of the recesses when the member and platen are in their operative position, but for not covering the recesses when the member and platen are in their inoperative positions. Finally, a precise length of tubing is removably mounted between the rollers and the platen so as to be squeezed in the gap by the rollers when the member and platen are in their operative position. The tubing is specially designed to have fittings of different size and/or shape formed at opposite ends of the precise length, which fittings nest in corresponding ones of the recesses only when the tubing is in a single orientation with respect to the member and platen. For all other orientations of the tubing, at least one of the fittings will not fully nest in an adjacent recess. The fittings coact with the element covering the corresponding recess to prevent relative movement between the member and platen from the inoperative to the operative position if the fitting is not fully nested in the recess. This assures that the member and platen are moved to their operative position only when the tubing therebetween is in the desired single orientation. Thus, even if the tubing is removed from the pump, the tubing, when reinserted in the pump, will be inserted in the same orientation each time.

The pump preferably includes at least one means for precisely adjusting the gap. For example, the position of the stop may be adjustable to precisely control the quantity of fluid which is pumped for each fractional rotation of the member. For a preferred embodiment, the stop is an eccentric which is rotated to adjust its position. The member may also for example be mounted so as to permit adjustment of its position relative to the platen when the member and platen are in the operative position and a gap tool may be provided for fitting in the gap during such adjustment.

Each of the fittings formed on the tubing may include a block formed as part of the tubing, with the blocks for the fittings preferably having a different size and/or shape to facilitate orientation of the tubing. At least one of the fittings may also include a stop of a hard material, such as a hard plastic, mounted to at least one side of the corresponding block. For preferred embodiments, at least one of the stops sandwiches the corresponding block therebetween. Further, in addition to the selected length of tubing between the blocks, for preferred embodiments, the tubing extends beyond the opposite end of each block for at least a sufficient distance to permit the barb of a connector fitting to be fitted therein, permitting the tubing to be attached to additional lengths of tubing or other attachments such as heat exchangers.

The foregoing and other objects, features and advantages of the invention will be apparent from the following more particular description of preferred embodiments of the invention as illustrated in the accompanying drawings.

IN THE DRAWINGS

FIG. 2 is a front view of the pump of FIG. 1 showing the pump in an inoperative position with a tube not inserted.

FIG. 3 is a front view of the pump in its operative position with a tube inserted and with some elements shown in phantom lines.

FIGS. 4A and 4B are partial sectional views of the pump illustrating how movement from the inoperative to the operative position is blocked when fittings are not fully nested and permitted when a fitting is fully nested, respectively.

FIG. 5 is a partially cut-away front view of the pump in its operative position.

FIG. 6 is a sectional side view taken along the line 6—6 in FIG. 5 and featuring the eccentric stop.

FIG. 7 is a rear plane view of the pump.

DETAILED DESCRIPTION

Figure 1:
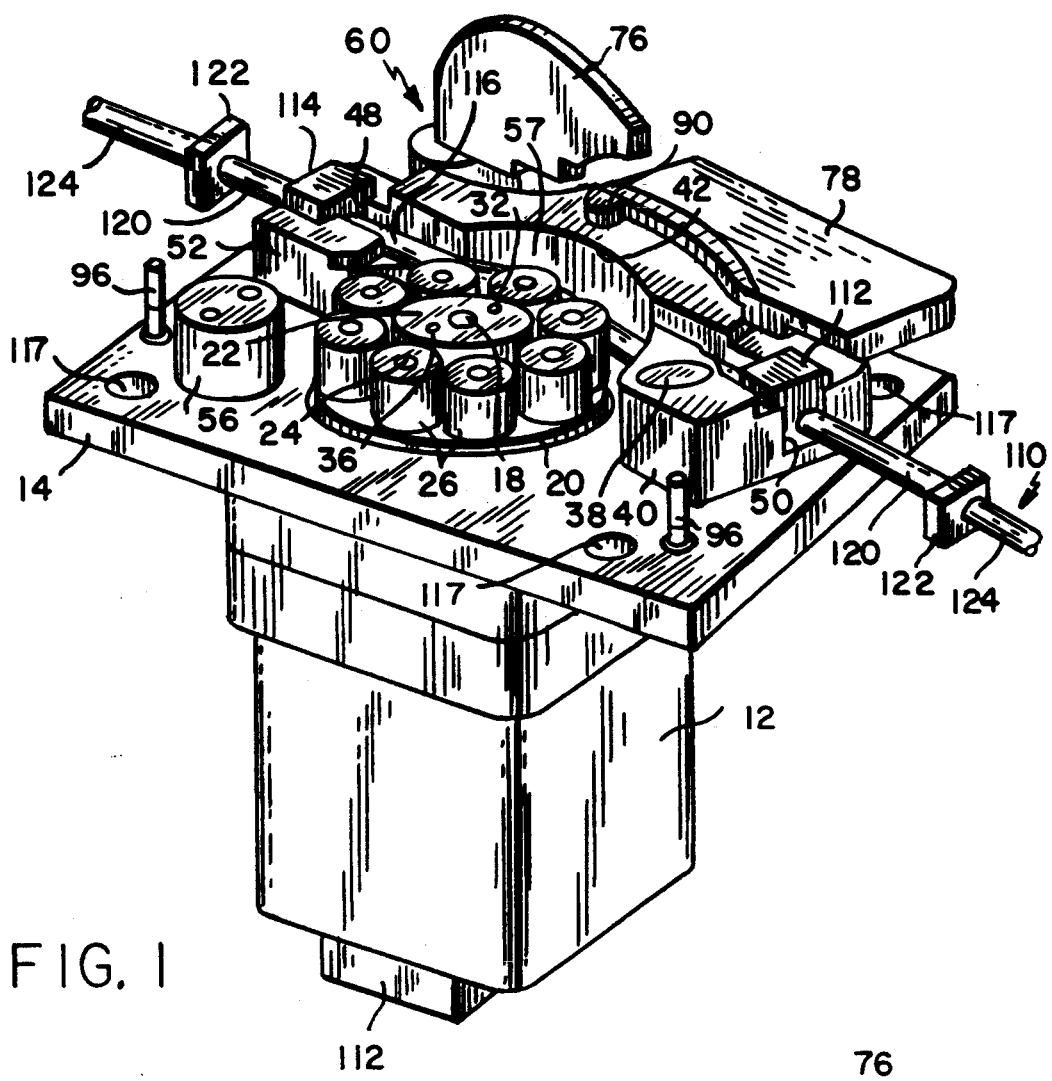
FIG. 1 is a front side perspective view of a peristaltic pump incorporating the teachings of this invention, the pump being shown in an inoperative position and with one cover removed.

Referring first to FIGS. 1-7, it is seen that the pump 10 for a preferred embodiment of the invention has a precision rotary motor 12 which may for example be a DC stepper motor or other rotary motor for which the number of revolutions may be precisely controlled and which has minimal "run out" or "wobble". The motor is attached to a mounting plate 14 by a pair of screws 16 (FIG. 7). The rotatable shaft 18 of motor 12 passes through a hole (not shown) in plate 14 and has a circular member 20 connected to the portion thereof extending through plate 14. Member 20 has a circular projection 22 at its center for the preferred embodiment which extends over shaft 18 and is secured thereto by pressure fit, gluing or other suitable means which will not cause any eccentricity between shaft 18 and member 20. As will be discussed later, any such eccentricity will cause undesired variations in the tube receiving gap and will adversely affect the precision of the pump. Member 20 also has a plurality of shafts 24 evenly spaced about a circle having a center at shaft 18, each of the shafts 24 extending perpendicular to the member 20. A roller 26 is rotatably mounted on each shaft 24 and is normally held in place by a cover plate 28 mounted over member 20 and rollers 24. Plate 28 has an alignment pin (not shown) on its underside which mates with a corresponding hole 32 on projection 22 and is held in place by a screw 34 (FIG. 5) which passes through plate 28 and is screwed into a corresponding opening 36 in projection 22.

Figure 3A:
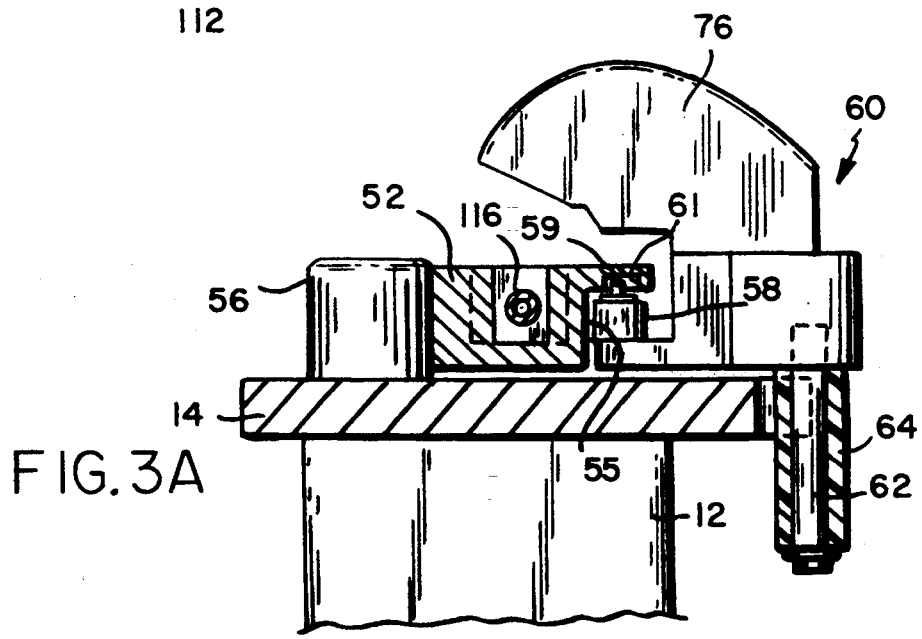
FIG. 3A is a sectional view taken along the line 3A—3A in FIG. 3.

Mounting plate 14 also has a post 38 secured to and projecting from the front face thereof. A platen 40 is mounted to pivot on post 38 between an inoperative position as shown in FIGS. 1 and 2 and an operative position as shown in FIGS. 3 and 5. Platen 40 has a curved surface 42 with a radius that substantially matches the maximum radius from shaft 18 to the outer edge of rollers 26, but is slightly greater. Platen 40 also has a pair of tube receiving grooves 44 and 46 (FIG. 2) each of which has a recess, 48 and 50, respectively, formed near the end thereof. Recesses 48 and 50 are different in size and/or shape so that a fitting which fits in at least one of such recesses will not fit in the other recess. As will be discussed in greater detail later, the recesses are preferably different in a sufficient number of ways that a fitting adapted to fit in each of the recesses will not fit or nest in the other recess.

Platen 40 also has a stop surface 52, a cam surface 54 with a detent notch or recess 55 formed near one end thereof, and a cam groove 61 formed in its underside. Stop surface 52 engages eccentric stop member 56 when platen 40 is moved to the operative position, thereby defining at least in part the size of the gap 57 between the rollers and platen surface 42.

Cam surface 54 coacts with a roller 58 on drive and latch member 60 and pin 59 on which roller 58 is mounted coacts with cam groove 61 to move platen 40 between its operative and inoperative positions as member 60 is rotated about a pivot post 62. Post 62 is fitted in a hole formed at one end of web 64 (FIG. 7), the other end of web 64 passing over and being secured to a post 66 mounted to plate 14. Web 64 may be held on post 66 by for example a locking washer or other suitable means. Post 62 has a spring 68 wrapped therearound which normally biases the post, and member 60 affixed thereto, in the counterclockwise direction (as viewed from the front in FIGS. 2 and 3). Web 64 also has a post 70 formed slightly below post 62 to which one end of a spring 72 is connected, the other end of spring 72 being connected to a post 74 fixed to plate 14 and extending from the rear thereof. Member 60 has a handle 76 which may be grasped between the thumb and forefinger of a user and used to pivot member 60, and thus platen 40, between the operative and inoperative positions.

Finally, platen 40 has a cover 78 mounted thereto. In particular, cover 78 has a shaft 80 (FIG. 3) extending from the rear thereof which fits into a corresponding opening 82 in platen 40 and is secured to the back thereof by a lock washer or other suitable means so as to permit cover 78 to pivot relative to the platen about shaft 80. A spring 84 wrapped around shaft 80 normally biases the cover in the counterclockwise direction to the position shown in FIG. 2. Rotation in a counterclockwise direction by cover 78 is limited by projection 86 extending from the rear of the cover contacting stop surface 88 of platen 40. Finally, cover 78 has a surface 90 which coacts with a camming surface 92 of a cover 94 to pivot cover 78 to the operative position shown in FIG. 3 in which this cover covers recess 50.

Cover 94 has openings (not shown) in its rear side which coact with posts 96 secured to and extending from the front face of plate 14 to orient and mount the cover. A screw 98 passing through mating holes in the cover and mounting plate 14 secures cover 94 to the mounting plate. Cover 94 has a raised portion 100 which overlies cover 28 to protect motor 12 and is operative to cover recess 48 when the elements are in their operative position.

As may be best seen in FIG. 6, eccentric stop member 56 has a larger countersink or hole 102, a smaller countersink or hole 104 and a shaft 106 projecting from the rear end thereof, which shaft is slightly off center. There is a screw hole 107 in the rear center of shaft 106. Holes 102 and 104 are used, preferably with a suitable tool (not shown), to orient the stop. Preferably, the stop is initially oriented to its normal position (i.e. in a position where rotation in one direction results in an increase in the size of the gap and rotation in the opposite direction results in a decrease in the size of the gap). The different sizes of holes 102 and 104 permit a user to visually determine the proper orientation for the stop when assembling the device. Stop 56 is secured to plate 14 by a screw 108 which passes through plate 14 and into hole 107. Screw 108 may be loosened to permit rotation of the stop.

In addition to the elements described above, pump 10 also has a drain 109 to permit any accumulated fluid to drain from the pump so as to protect the motor, electrical connectors 113 for permitting desired electrical connections to be made to motor 12, and screws 115 which pass through corresponding holes 117 at the corners of plate 14 to permit the pump to be mounted to a frame, chassis or housing of equipment with which the pump is to be utilized.

The final elements of the pump are tubes 110 which are used in conjunction with pump 10. Each tube 110 has a pair of fittings 112 and 114 with a precise length 116 of tubing therebetween, which tubing is to fit in the gap 57 between rollers 26 and platen surface 42. For preferred embodiments, a portion 120 of tubing extends beyond each of the fittings 112 and 114. For each tube portion 120, a connector fitting 122 is provided which has a barb at one end fitting into the corresponding tube section 120 and a barb at its other end which fits into a length of extension tubing 124.

Figure 8A:
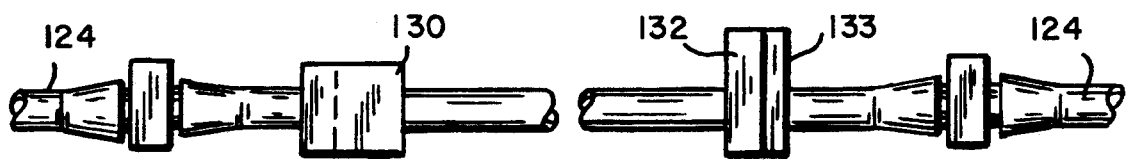
FIGS. 8A, 9A, 10A and 11A are enlarged top views of various embodiments of tubing suitable for use with a pump of this invention illustrating various fittings and placement of fittings relative to the tubing.
Figure 8B:
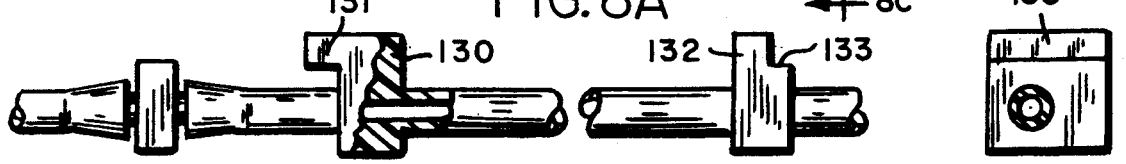
FIGS. 8B, 9B, 10B and 11B are partially sectioned side views of the tubing embodiments shown in FIGS. 8A, 9A, 10A and 11A, respectively.
Figure 8C:
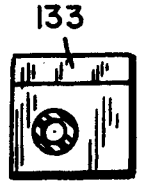
FIGS. 8C, 9C, 10C and 11C are end views of the tubing embodiments taken along the line 8C—8C of FIGS. 8B, 9C—9C of FIG. 9B, 10C—10C of FIG. 10B and 11C—11C of FIG. 11B, respectively.

For preferred embodiments, tubing 116 and 120 are formed of a silicon rubber or other suitable flexible material and each fixture 112-114 includes a block molded as part of the tubing. FIGS. 8A-8C illustrate fittings which includes only blocks 130-132. As with all embodiments of the invention, the blocks 130 and 132 are of different size and/or shape (preferably both) and are further shaped so as to fit in only a single one of the recesses 48 and 50 and to fully nest in such recess only for a single orientation of the block in the corresponding recess. In addition to relative length, width and thickness of the blocks, the desired nesting of the fitting in only one orientation may be accomplished by providing notches, projections, flanges or other structural variations on each block which mate with corresponding projections, indentations, ridges or the like on recesses 48 and 50 so as to permit the blocks to be inserted with only a single orientation. Examples of such shape variations in the blocks are shown in the various FIGS. 8A-11C. For example, in FIGS. 8A-8C, a flange 131 is shown for the block 130 and a recess or indentation 133 is shown for the block 132.

While the desired single permitted orientation may be achieved with fittings formed of blocks 130,132 alone, such fittings have two potential disadvantages. First, the rubber tends to grip the walls of the corresponding recess, complicating insertion and withdrawal of the fittings, particularly for a relatively close fit. Since it is desirable that these operations be performed quickly, such sticking or grabbing is undesirable. Second, as is shown in FIGS. 4A and 4B, and as will be discussed in greater detail later, one function of the fittings is to inhibit movement from the inoperative to the operative position when either one of the fittings is not fully nested or seated. This assures that the pump cannot be operated unless tubing 110 has been inserted with the proper orientation. Assuring that tubing 110 is always inserted with the same orientation means that the length and shape of the tubing will be the same regardless of the number of times the tubing has been inserted and removed and assures against any variations caused by the tubing being inserted with a different orientation for different uses. The single acceptable orientation also assures that any seam in the tubing which is present for some tubing construction techniques is on a portion of the tube which is not contacted by either rollers 26 or platen 40 so that the existence of such seams does not impact the accuracy of fluid delivery from the pump.

However, the blockage of platen movement is caused by any portion of the fitting projecting above the recess interacting with the cover for such recess to prevent the cover from passing over the recess and thus to prevent completion of movement from the inoperative to the operative position. However, silicon rubber and other flexible tubing materials are relatively soft and it is therefore possible, when the blocks are formed of such material, for the blocks to deform and permit movement to the operative position even when a fitting is not fully nested. Therefore, if the configuration of FIGS. 8A-8C is to be utilized in accordance with preferred embodiments of the invention, the tubing, or at least the block portion thereof, must be formed of a harder rubber or other material which is not easily deformed. However, harder rubber tends to not work well as a peristaltic pumping medium.

Figure 9A:
Figure 9B:
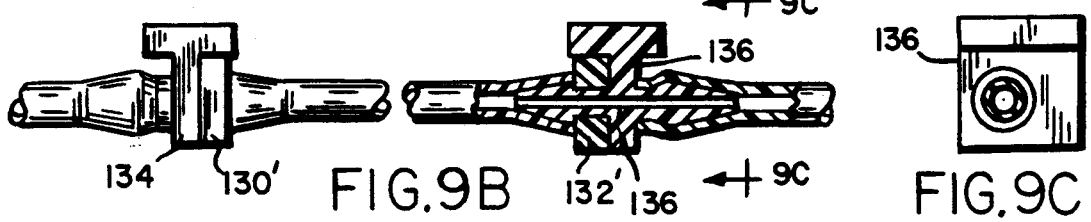
Figure 9C:
Figure 10A:
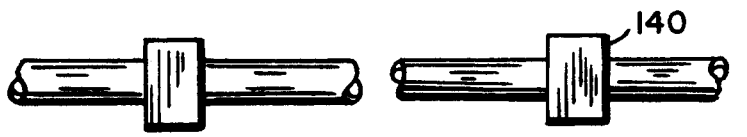
Figure 10B:
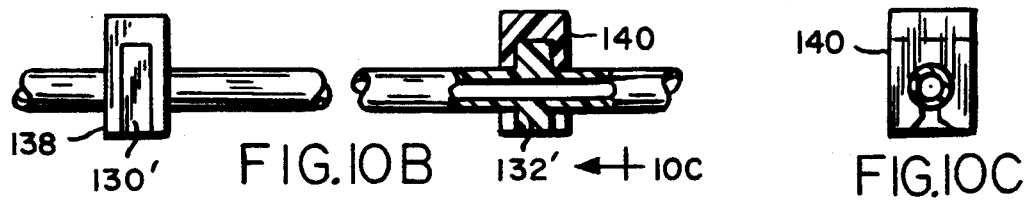
Figure 10C:
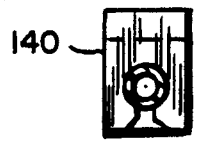
Figure 11A:
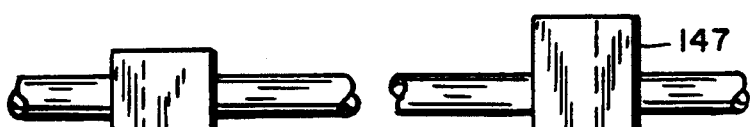
Figure 11B:
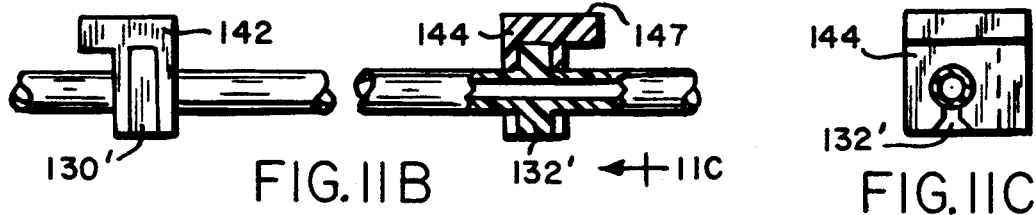
Figure 11C:
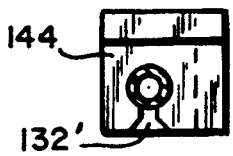

Therefore, as shown in FIGS. 9A-11C, a hard plastic stop is preferably fitted over or attached to a portion of each block to form the fittings. The (as shown in FIGS. 9A-9C for 134 and 136) maybe snapped over tubing 116 and glued or otherwise secured to the block (130'-132') to form the fitting, or, as shown in FIGS. 10A-11C, the stop (138, 140 or 142, 144) may snap over the tubing and sandwich the corresponding block. FIG. 11C illustrates one of the stops 144 having additional material on one side rendering the stop asymmetric so as to facilitate the fitting of the fixture embodying the stop in only one of the recesses and in only a single orientation. Other variations including projections, recesses, flanges 145,147 and the like can be provided on the stops to facilitate single-orientation insertion in corresponding recesses.

The stops perform a number of functions. First, they protect the blocks which, as previously indicated, may be formed of a soft silicon rubber. Second, they have smooth surfaces which makes the fixtures easier and thus quicker to insert and remove into the corresponding recesses. Third, and perhaps most important, they assure that movement to an operative position for the pump cannot occur unless both fixtures are fully seated in their corresponding recess. This prevents incorrect volumes being delivered and possible wrong answers being given by the analyzer. If no volume is delivered, the system will give "No Result Detected" as an answer and the operator will know something is wrong.

In calibration of the pump, which is done during assembly and is not intended to be done by a user, the first step is to assure that eccentric stop 56 is properly oriented, with for example the larger hole 102 to the right and the holes horizontally aligned as shown in FIGS. 1-3 and 5. The next step is to fit the gap tool in the space between rollers 26 and platen 40, to loosen screws and to then use handle 76 to rotate drive and latch member 60 in the clockwise direction to move the pump to its operative position. Since there is no tubing 110 in the pump at this time, seating of fixtures 112, 114 is not a factor. The position of the motor assembly including circular member 20 affixed to the end thereof, is then adjusted so that the rollers 26 press against the nondeformable tool to establish the desired gap 57 between the rollers and the platen. Screws 16 are then tightened.

However, while pump 10 is precision designed, it is still possible that there may be slight variations in the radius of platen surface 42, in the rollers, in the shape of member 20 or a slight eccentricity in the mounting of this member so that the desired volume of fluid per revolution of the pump, for example 50 microliters per revolution, is not being achieved. The exact volume being pumped by the pump can be determined by putting a length of tubing 110 in pump 10, moving the pump to its operative position, running motor 12 for a known number of whole and/or fractional revolutions and measuring the volume of fluid pumped. To the extent the volume of fluid actually pumped is greater than or less than the desired volume, screw 108 may be loosened and eccentric stop 56 rotated slightly in the proper direction to either slightly enlarge or slightly reduce the size of the gap in order to effect a slight increase or decrease, respectively, in volume pumped. Several iterations of measurement and adjustment may be required until the pump is producing the exact volume desired within for example a few microliters.

When the pump has been calibrated it is ready to be sent to a user and to be utilized. For utilization, a piece of tubing 110 having fittings 112 and 114 which are sized and shaped to fit and nest in recesses 48 and 50, respectively, is fitted with the section 116 in the space between rollers 26 and platen 40 with the pump in its inoperative position. When each of the fixtures has been fully nested in its corresponding recess, tubing 116 is properly oriented in the gap and handle 76 may be manually operated by a user to move drive and latch member 60 in the clockwise direction. This causes roller 58 on member 60 to ride up cam surface 54 of platen 40 and pin 59 to move in cam groove 61 pivoting the platen counterclockwise about post 38 toward its operative position. Since the fixtures are fully nested, upper fixture 114 clears the front upper surface of cover 94. Surface 90 of cover 78 also engages cam surface 92 of cover 94 rotating cover 78 clockwise about pivot 80 against the force of spring 84. Since fixture 112 is also fully nested in recess 50 at this time, cover 78 passes over the fixture as a result of this rotation. When platen 40 has been fully moved to the operative position, roller 58 under pressure from spring 72 drops into recess 55 in cam surface 54. This locks the pump in its operative position.

When the pump is locked in its operative position as shown in FIGS. 3 and 5, tube section 116 is pinched in gap 57 between rollers 26 and platen surface 42, with there being a precise quantity of fluid pinched in tubing 116 between each pair of adjacent rollers. When motor 12 is turned on to rotate rollers 26, the fluid trapped between each pair of adjacent rollers is moved with the rollers along tubing 116 from fitting 112 to fitting 114. This fluid forces fluid above or ahead of it in tubing 116 and into the tubing 120 and 124 therebeyond in the pump. As the fluid is pushed forward, a vacuum is created behind it in tubing 110 which draws additional fluid into the tubing. A pumping action is thus accomplished. However, because the length and orientation of tubing in gap 57 is precisely controlled and the size of the gap is precisely controlled, the pump is capable of providing precise quantities of fluid. For example, if the pump is calibrated to deliver 50 microliters for a complete revolution, 50/8 or 6.25 microliters are delivered by the pump for each $\frac{1}{8}$th revolution thereof, permitting precise delivery of fluid within the microliter range.

When the pumping operation from a given reservoir to an end location, for example a cuvette, has been completed, the appropriate ends of tubing 110 may be moved to a new reservoir and a new receiving receptacle or, to avoid contamination, the pump may be moved to its inoperative position and tubing 110 replaced before a new pumping operation is performed. In the latter event, handle 76 is operated to move drive and latch member 60 in the counterclockwise direction. This permits roller 58 to disengage from recess 55 as the camming action of the roller against the walls of the recess overcome the spring force of spring 72. Roller 58 then rides down camming surface 42 under the action of spring 68, and pin 59 moves in camming groove 61, these movements combining to cam platen 42 to rotate in the clockwise direction to its inoperative position. As surface 90 rides down camming surface 92 and ultimately disengages therefrom, cover 78 is also returned to its inoperative position shown in FIG. 2 by the action of spring 84. Once the pump is fully returned to its inoperative position, tube section 110 may be removed and a new tube section fitted in the pump in its place. The pump is then moved to its operative position in the manner previously discussed and the process repeated.

When a section of tubing 110 is removed, it may either be discarded, sent to an appropriate location for cleaning or sterilization, which can normally be easily accomplished even with viscous fluids passing therethrough, or may be retained and reinserted in the pump the next time pumping is required from the same reservoir. For example, if reagents are being pumped, the same section of tubing may be used for pumping reagents into successive cuvettes. However, a section of tubing is slightly deformed when it is used in pump 10 and it is therefore important that the tubing be reinserted in the pump in the same precise orientation each time it is used in order to assure precise pumping. The coaction of fittings 112 and 114 with recesses 48 and 50 assure that this occurs in the manner previously described for each insertion of a given tubing section 110.

A peristaltic pump is thus provided which is easily used with all types of fluids, including viscous fluids, while still permitting precise quantities of fluid to be pumped. While the invention has been particularly described above with reference to a preferred embodiment for the pump and preferred embodiments for the various tubing sections, it is apparent that these embodiments are for purposes of illustration only and that other mechanisms known in the art could be utilized for operating the pump, for moving the pump between its operative and inoperative positions, for blocking movement from the inoperative to the operative position when a fixture is not fully seated and for performing the various adjustments. For example, while only platen 40 is pivoted to move the pump between the operative and inoperative positions, and this mode of operation is preferred, the pump could be moved to its operative position by moving member 20 in some appropriate way or by moving both member 20 and platen 40 toward each other. The invention might, with suitable modifications, also be practiced with other peristaltic pump designs. Further, while representative fixtures have been shown in the drawings, it is apparent that other fixture configurations falling within the teachings of the invention might also be utilized. Thus, while the invention has been particularly shown and described above with reference to preferred embodiments, the foregoing and other changes in form and detail may be made therein by one skilled in the art without departing from the spirit and scope of the invention.

What is claimed is:

1. A precision peristaltic pump comprising:
   a plurality of rollers mounted at spaced intervals along the periphery of a circular member;
   a motor for rotating said circular member through a precise number of fractional rotations;
   a platen having a curved surface facing said rollers and shaped with a curve complementary to that of said member mounted rollers;
   means for mounting both said member and said platen such that they are movable relative to each other between an operative position where there is a small precise gap between the platen and a selected number of adjacent rollers and an inoperative position where there is a predetermined larger spacing between the platen and rollers, said gap having an upper and a lower end;
   first and second recesses formed on said upper and said lower ends, respectively, of said gap, said recesses being shaped differently from each other so that a complementary fitting which fits at least one of said recesses will not fit in the other;
   an element covering each of said recesses when the member and platen are in their operative position, but not covering the recesses when the member and platen are in their inoperative position; and
   a precise length of tubing removably mounted between said rollers and said platen so as to be squeezed in said gap by said rollers when said member and platen are in their operative position, said tubing having fittings of different configuration formed at opposite ends of said length, wherein said fittings consist of sections of harder material than the tubing, which fittings each nest in a corresponding one of said recesses only when said tubing is in a single orientation with respect to the member and platen, said fittings coacting with the elements covering the corresponding recess to prevent movement by said means for mounting from said inoperative to said operative positions if the fitting is not fully nested in the recess, whereby said member and platen may be moved to their operative position when said tubing is therebetween only when the tubing is in said single orientation.

2. A pump as claimed in claim 1 wherein only said platen is moved to move the member and platen between their operative and inoperative positions, and an adjustable stop for precisely defining the operative positions for the platen, said stop being an eccentric which is rotated to adjust its position.

3. A pump as claimed in claim 1 wherein each of said fittings includes a block formed as part of said tubing.

4. A pump as claimed in claim 3 wherein the blocks for said fittings have at least one of a different size and a different shape.

5. A pump as claimed in claim 3 wherein each block has a first side adjacent the precise length of tubing and a second side opposite the first side, and wherein at least one of said fittings includes a stop of a hard material mounted to at least one of said sides of the corresponding block.

6. A pump as claimed in claim 5 wherein at least one of said stops sandwiches the corresponding block therebetween.

7. A pump as claimed in claim 5 wherein the stops for said fittings have at least one of a different size and a different shape.

8. A pump as claimed in claim 3 wherein, in addition to the selected length of tubing between said blocks, said tubing extends beyond the opposite end of each block for at least a sufficient distance to permit a barb for a connector fitting to fit therein.

9. A pump as claimed in claim 1 wherein the element covering each recess and the recess are mounted for relative movement between a covered and uncovered position, said relative movement being a sliding movement of the cover over the top of the recess, whereby any portion of a fitting projecting above the top of a recess prevents relative movement of the element and recess to a covered position.

10. A tubing for use in a peristaltic pump having a tubing receiving gap with first and second recesses being formed on opposite ends, respectively, of said gap, said recesses being shaped differently from each other so that a complementary fitting which fits in at least one of said recesses will not fit in the other, said tubing comprising:
    a first fitting formed in said tubing; and
    a second fitting formed in said tubing, said second fitting being spaced from said first fitting to define a precise length of said tubing therebetween, and said second fitting having at least one of a different size and shape than said first fitting, wherein said fittings consist of sections of harder material than the tubing, the respective sizes and shapes of said fittings being such that said fittings nest in corresponding ones of said recesses only when said tubing is in a single orientation in said gap.

11. A tubing as claimed in claim 10 wherein each of said fittings includes a block formed as part of said tubing.

12. A tubing as claimed in claim 11 wherein the block for each of said fittings has at least one of a different size and a different shape.

13. A tubing as claimed in claim 11 wherein at least one of said fittings includes a stop of a hard material mounted to at least one side of the corresponding block.

14. A tubing as claimed in claim 13 wherein at least one of said stops sandwiches the corresponding block therebetween.

15. A tubing as claimed in claim 13 wherein the stops for said fittings have at least one of a different size and a different shape.

16. A tubing as claimed in claim 11 wherein, in addition to the selected length of tubing between said blocks, said tubing extends beyond the opposite end of each block for at least a sufficient distance to permit a barb to be fitted therein.

* * * * *